United States Patent [19]

Reinhold, Jr. et al.

[11] Patent Number: 5,373,851
[45] Date of Patent: Dec. 20, 1994

[54] SPECIALIZED PEAK FLOW METER

[75] Inventors: Herbert E. Reinhold, Jr., Rockville; Martin D. Valentine, Baltimore; O. Napoleon Monroe, Bethesda, all of Md.

[73] Assignees: Brunswick Biomedical Corporation, Marlboro, Mass.; The Johns Hopkins University, Baltimore, Md.

[21] Appl. No.: 47,495

[22] Filed: Apr. 19, 1993

[51] Int. Cl.$^5$ .............................................. A61B 5/091
[52] U.S. Cl. ............................... 128/716; 128/725; 482/13
[58] Field of Search ................... 128/725–730, 128/716; 73/861.71; 340/611; 482/13

[56]  References Cited

U.S. PATENT DOCUMENTS

| | | |
|---|---|---|
| D. 254,443 | 3/1980 | Adams . |
| 3,577,984 | 5/1971 | Levy . |
| 3,608,546 | 9/1971 | Shinn . |
| 3,645,133 | 2/1972 | Simeth . |
| 3,726,270 | 4/1973 | Griffis . |
| 3,726,271 | 5/1973 | Mondshine . |
| 3,896,792 | 7/1975 | Vail . |
| 3,924,612 | 12/1975 | Dempster . |
| 3,958,565 | 5/1976 | Wright . |
| 3,991,304 | 11/1976 | Hillsman . |
| 4,068,096 | 1/1978 | Rattenborg . |
| 4,231,375 | 11/1980 | Boehringer . |
| 4,271,701 | 6/1981 | Dempster . |
| 4,296,756 | 10/1981 | Dunning et al. ............... 128/725 |
| 4,391,283 | 7/1983 | Sharpless . |
| 4,425,805 | 1/1984 | Ogura . |
| 4,444,201 | 4/1984 | Itoh . |
| 4,495,944 | 1/1985 | Brisson . |
| 4,635,647 | 1/1987 | Choski . |
| 4,644,958 | 2/1987 | Brisson . |
| 4,727,886 | 3/1988 | Conrardy . |
| 4,736,750 | 4/1988 | Valdespino . |
| 4,764,111 | 8/1988 | Knierim ............................ 433/5 |
| 4,765,342 | 8/1988 | Urman . |
| 4,768,520 | 9/1988 | Varraux et al. ............... 128/725 |
| 4,796,639 | 1/1989 | Snow . |
| 4,803,997 | 2/1989 | Bowman . |
| 4,807,614 | 2/1989 | van der Smissen . |
| 4,981,295 | 1/1991 | Belman . |
| 4,984,158 | 1/1991 | Hillsman . |
| 5,056,513 | 10/1991 | Boutin . |
| 5,058,601 | 10/1991 | Riker ............................... 128/725 |
| 5,063,938 | 11/1991 | Beck . |
| 5,086,777 | 2/1992 | Hishii ............................... 128/675 |
| 5,111,827 | 5/1992 | Rantala ............................ 128/725 |
| 5,137,026 | 8/1992 | Waterson et al. ............... 128/725 |
| 5,211,180 | 5/1993 | Wright et al. ................... 128/725 |

FOREIGN PATENT DOCUMENTS

| | | |
|---|---|---|
| 1224387 | 3/1971 | United Kingdom . |
| 1338501 | 11/1973 | United Kingdom . |
| 1500627 | 2/1978 | United Kingdom . |
| 1521412 | 8/1978 | United Kingdom . |
| 2238130 | 5/1991 | United Kingdom ............ 128/725 |
| 2238389 | 5/1991 | United Kingdom ............ 128/725 |

*Primary Examiner*—Lee S. Cohen
*Assistant Examiner*—Robert L. Nasser, Jr.
*Attorney, Agent, or Firm*—Cushman Darby & Cushman

[57]  ABSTRACT

The present invention provides a peak flow meter which facilitates a subject's compliance with the use thereof. In one embodiment, the peak flow meter provides an alarm for indicating that the subject is due for a peak expiratory flow rate evaluation when the subject has failed to use the peak flow meter after a predetermined period of time. In another embodiment, the peak flow meter is provided with circuitry which derives a data result corresponding to the peak expiratory flow rate of air blown into the peak flow meter for a number of blows. A first comparator determines the best data result within the number of blows and a memory stores each best data result. A second comparator compares each best data result to a specified value and provides an enabling signal to an alarm when a best data result is a predetermined amount lower than the specified value. To provide an incentive for the subject to blow as hard as possible into the peak flow meter, the a comparator may also compare each data result to the previous data result and provide an indication when the most recent data result is greater than the preceding data result.

25 Claims, 4 Drawing Sheets

SPECIALIZED PEAK FLOW METER

This invention relates to pulmonary function measuring devices and more particularly to peak flow meters. Peak flow meters are used in the medical field for the measurement of human respiratory capabilities and are especially useful for asthma and emphysema patients. Conventional peak flow meters are capable of achieving precise measurements of varying parameters defining the subject's peak expiratory flow rate (PEFR), which is the greatest flow velocity that can be obtained during forced expiration starting with fully inflated lungs. A detected decrease in PEFR may signify the onset of a potentially harmful pulmonary airflow obstruction.

While peak flow measurements are often performed by medical personnel using highly sophisticated equipment incorporating, for example, computer analyses and chart recorders, experts in the medical field recommend regular home use of peak flow meters for continuous monitoring and an early detection of a decrease in PEFR. Such early detection enables a respiratory subject to seek treatment before respiratory problems worsen. In addition, home monitoring may help patients determine which specific allergens or workplace exposures exacerbate their symptoms. Therefore, the present invention provides an inexpensive, easy to use peak flow meter which provides accurate readings and is suited for in-home use.

A primary limitation of the accuracy of peak flow meter monitoring, however, is that it is effort dependant. Effective respiratory monitoring depends largely on the patient's willingness to use the peak flow meter on a regular basis. A typical respiratory patient is required to monitor PEFR on a regular daily basis, although more or less frequent measurements may be required depending upon the particular patient's respiratory condition. Because such frequent peak flow measurements can become tedious, many patients become lax in their compliance with using the peak flow meter. Other patients may simply forget to use the instrument. Therefore, there exists a need for a peak flow meter which will effectively enhance patient compliance.

Therefore, it is an object of the present invention to fulfill the need expressed above. In accordance with the principles of the present invention, this objective is achieved by providing a peak flow meter which provides a prompt for facilitating a subject's compliance with the periodic use thereof. The peak flow meter includes a conduit through which air can be blown by the subject and a means for evaluating a peak expiratory flow rate attained by the subject when the subject blows into the conduit. An indicating means is provided for indicating that the subject is due for a peak expiratory flow rate evaluation when the subject fails to blow into said conduit after a predetermined time period since the subject's last peak expiratory flow rate evaluation.

The effective use of currently available peak flow meters is also limited by the fact that they merely provide the patient with a numerical measurement reading corresponding to the peak expiratory flow rate. Unless tedious monitoring and recording of data are performed, the numerical reading is a meaningless number rather than a clear indication of whether the patient is in need of medical attention.

Thus, another object of the present invention is to provide a peak flow meter having an alarm means for providing an indication to the subject that the measured PEFR is a predetermined amount lower than a specified value. In this embodiment, the peak flow meter includes a conduit through which air can be blown by a subject and a restriction means causing air blown into the conduit to escape at a restricted rate therefrom and create a pressure rise therein. A pressure sensing means generates an electrical signal corresponding to the pressure rise within the conduit, and a data processing means processes the electrical signal to derive a data result corresponding to the peak expiratory flow rate of the air blown into the conduit. A comparison means compares the data result to a specified value and generates an output signal when the data result is a predetermined amount lower than the specified value. Finally, an alarm means, in response to the output signal, indicates when a data result is a predetermined amount lower than the specified value.

Since PEFR is the greatest flow velocity that can be obtained during forced expiration, a subject's failure to exhale with maximum effort will result in inaccurate PEFR readings. It is therefore advantageous to take several measurements; the best of those measurements being used in establishing an accurate PEFR result. Thus, in another embodiment, there is provided a peak flow meter having a conduit through which air can be blown by a subject and a restriction means causing air blown into the conduit to escape at a restricted rate therefrom and create a pressure rise therein. A pressure sensing means generates an electrical signal corresponding to the pressure rise within the conduit each time the subject blows into the conduit. A data processing means processes each electrical signal to derive data results corresponding the peak expiratory flow rates of air blown into the conduit for a number of blows by the subject. A first comparison means compares data results to one another for the number of blows by the subject and derives a best data result among them. This best data result corresponds to a best peak expiratory flow rate attained by the subject in the number of blows. Next, a second comparison means generates an output signal if the best data result is a predetermined amount lower than a specified value. Finally, an alarm means, in response to the output signal, generates an indication if the best data result is a predetermined amount lower than the specified value.

It is also advantageous to further provide a means of inducing the subject to exhale with maximum effort in order to obtain an accurate best PEFR result within the a set of PEFR measurements. Such inducement can be accomplished by providing a peak flow meter having a conduit through which air can be blown by a subject and a restricting means for causing air blown into the conduit to escape at a restricted rate therefrom and create a pressure rise therein. A pressure sensing means generates an electrical signal corresponding to the pressure rise within the conduit each time the subject blows into the conduit. A data processing means processes each electrical signal and derives data results corresponding to the peak expiratory flow rates of air blown into the conduit for a number of blows by the subject. A comparison means compares successive data results derived by the data processing means and generates a greater indication signal when a most recent data result is greater than a preceding data result. Finally, an indication means, responsive to the greater indication signal, provides an indication to the subject when the most recent data result is greater than the preceding data result. This provides a respiratory patient a goal or incentive to exceed the preceding PEFR measurement so that a truly best PEFR measurement is attained.

Another object of the present invention addresses the problem of cross-contamination of peak flow meters between patients. Peak flow meters are difficult to sterilize because they contain electronic and/or moving parts which are easily damaged. While most peak flow meters provide a removable mouthpiece which can be separately sterilized, the electronic or moving components remain contaminated by human expiration and may become a potential source of disease.

The present invention resolves the aforementioned problem by providing a means of measuring the peak expiratory flow rate of the subject without exposing the electrical components of the pressure transducer directly to human expiration. A flexible element is provided in air communication with the conduit of a peak flow meter which flexes in response to a pressure rise in the conduit. A chamber portion of the pressure transducer has an inner space, which is in airtight communication with the flexible element. Flexing of the flexible element towards the inner air space creates a pressure rise in the chamber corresponding to a pressure rise generated in the conduit when a subject blows therein. The pressure transducer is thus able to provide a pressure measurement corresponding to the pressure within the conduit without direct exposure to the air blown therein.

DETAILED DESCRIPTION OF THE INVENTION

Figure 1:
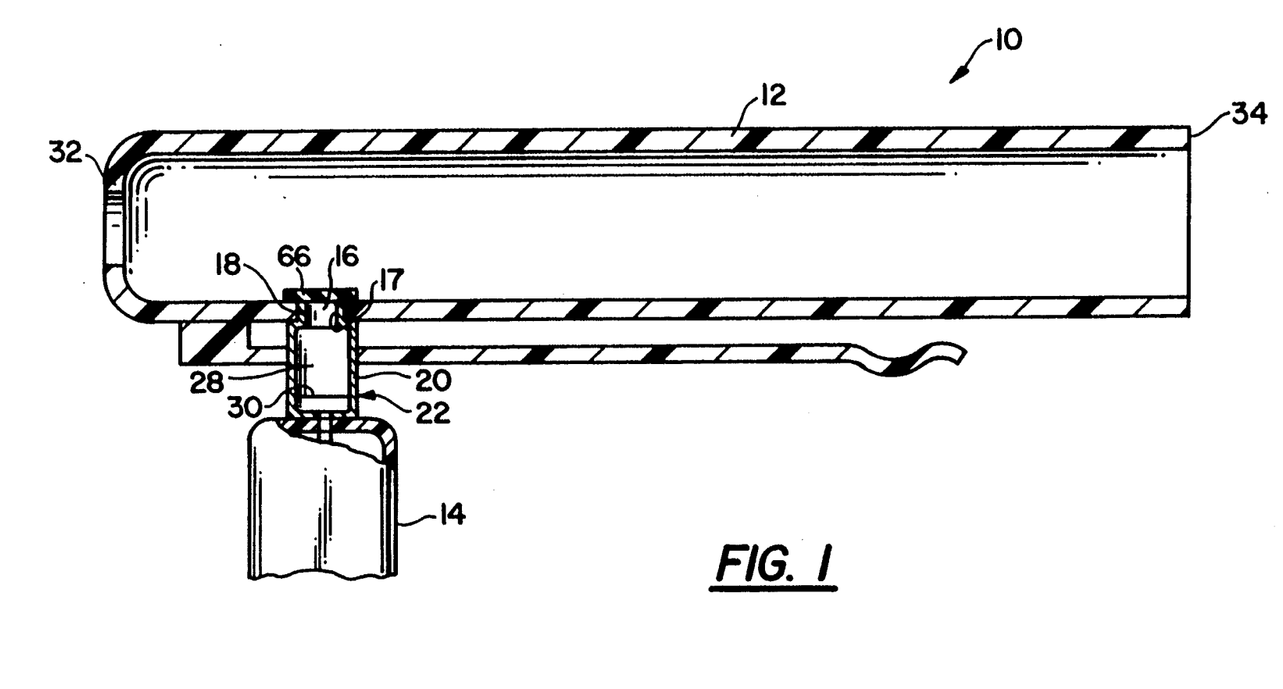
FIG. 1 is a longitudinal sectional view of the peak flow meter embodying the principles of the present invention.

Referring, more particularly, to the drawings, there is shown in FIG. 1 thereof a peak flow meter, generally indicated at 10, which embodies the principles of the present invention. The peak flow meter includes two basic assemblies: (1) a conduit, indicated at 12; and (2) an electronic housing, indicated at 14. Conduit 12 has an orifice 16, seen more clearly in FIG. 3, in which conduit 12 and electronic housing 14 are disassembled and flexible element 66 has been removed.

Referring back to FIG. 1, it can be appreciated that conduit 12 is mounted on the electronic housing 14. The electronic housing 14 carries peak expiratory flow measuring means including a pressure transducer 22 and circuitry means cooperable with the transducer to derive the peak expiratory flow rate of a subject. It can be appreciated that pressure transducer 22 includes a chamber 20, a chamber opening 18, an inner air space 28, a diaphragm 30, and electronic circuitry, not shown in the figures, which generates electrical signals in response to flexing of diaphragm 30. Chamber opening 18 securely fits into orifice 16 of conduit 12 to form an airtight seal with the edge wall 17, seen more clearly in FIG. 3, surrounding orifice 16. The airtight seal between the edge wall 17 surrounding orifice 16 and chamber opening 18 may be formed merely by a close tolerance between the diameter of orifice 16 and the outer diameter of chamber opening 18. Alternatively, the seal may be in the form of a fitted connection such as a threaded connection, or in some other form.

When a subject places his or her lips around inlet 34 at one end of conduit 12 and blows, a pressure rise is created within conduit 12. To enhance the pressure rise, a restriction 32 is placed in the conduit at the end opposite inlet 34. Restriction 32 is, in the most preferred embodiment, a sudden narrowing in the air passage of conduit 12 as shown in FIG. 1. While restriction 32 need not be positioned at the furthest extremity from inlet 34 of conduit 12, as in FIG. 3, it must be positioned such that orifice 16 is disposed between inlet 34 and restriction 32 so that pressure transducer 22 receives the full effect of the pressure rise. In response to the pressure rise in conduit 12, diaphragm 30 of pressure transducer 22 acts as a pressure sensor and causes pressure transducer 22 to generate an electrical signal corresponding to the magnitude of the pressure rise.

The conduit 12 may be provided with flexible element 66 which sealingly covers orifice 16. The purpose of flexible element 66 is to prevent moisture and germ contamination from entering chamber 20 of pressure transducer 22. If moisture and/or mucus are permitted to enter chamber 20, germs and bacteria may begin to inhabit chamber 20 and become a source of disease. By sealing orifice 16 with flexible element 66, human expiration is prevented from entering chamber and, as a result, chamber 20 is kept sterile. Since conduit 12 can be separated from electronic housing 14 and contains no electronic circuitry, it can be effectively sterilized.

Although flexible element 66 prevents human expiration from entering chamber 20, an accurate pressure reading of air blown into the chamber can nevertheless be obtained. When flexible element 66 is in place, it will flex towards inner space 28 of chamber 20 in response to a pressure rise in conduit 12. Since the inner air space 28 of chamber 20 is in airtight communication with flexible element 66, such flexing towards said inner air space 28 of chamber 20 creates a pressure rise in chamber 20 which is substantially proportional to the pressure rise in conduit 12. Pressure transducer 22 is calibrated accordingly to generate an electrical signal which can be converted into a digital reading indicative of the peak expiratory flow rate of the subject.

It can be appreciated that flexible element 66, in the broader aspect of the invention, need not be sealed to orifice 16. Flexible element 66 may, instead, be sealed to chamber opening 18 and still have the same pressure transmitting effects into chamber 20. Alternatively, flexible element 66 need not be sealed to either orifice 16 or chamber opening 18, but merely sandwiched between the outer diameter of chamber opening 18 and the surrounding edge wall 17 of orifice 16.

Figure 2:
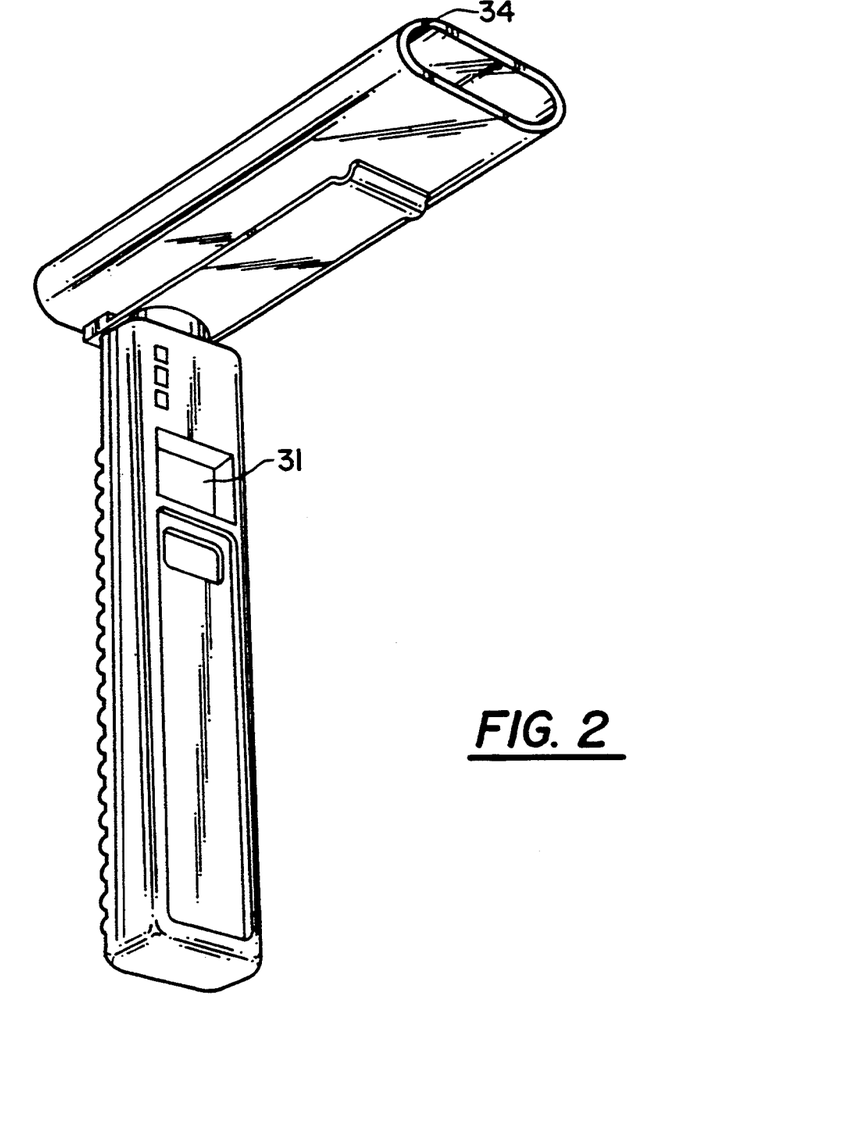
FIG. 2 is a perspective view of a peak flow meter embodying the principles of the present invention.

Referring now to FIG. 2, it can be seen that the peak flow meter is provided with an LED display 31. This display provides PEFR measurements to the subject. The display may also provide warning indications in accordance with some of the following embodiments.

Figure 3:
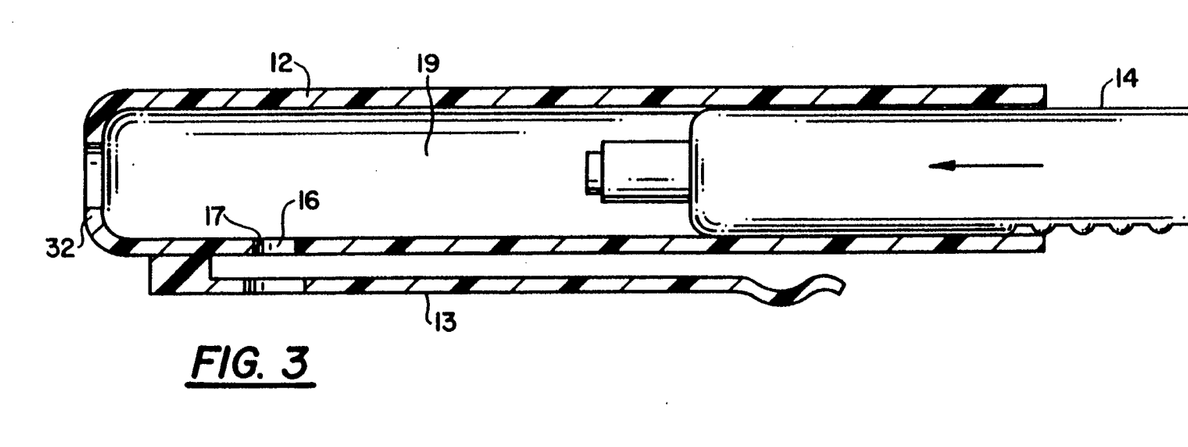
FIG. 3 is a longitudinal sectional view of a disassembled peak flow meter embodying the principles of the present invention.

Referring now to FIG. 3, the peak flow meter is shown in its disassembled storage condition. Since a further limitation to the regular use of peak flow meters stems from the fact that many of the commercial devices are bulky and do not lend themselves to being carried by the patient, a further object of the present invention is to provide a peak flow meter which is compact in its storage condition. Therefore, the peak flow meter of the present invention is disassembleable into two separate components, one of which is capable of receiving the other when the peak flow meter is not in use, thereby forming a compact, easily transportable device. To provide this smaller storage package, the inner space 19 of conduit 12 is large enough to receive the electronic housing 14. A clip member 13 is fixed to the exterior of conduit 12 to enable the peak flow meter to be secured to a shirt pocket or the like when the peak flow meter is not in use.

Figure 4A:
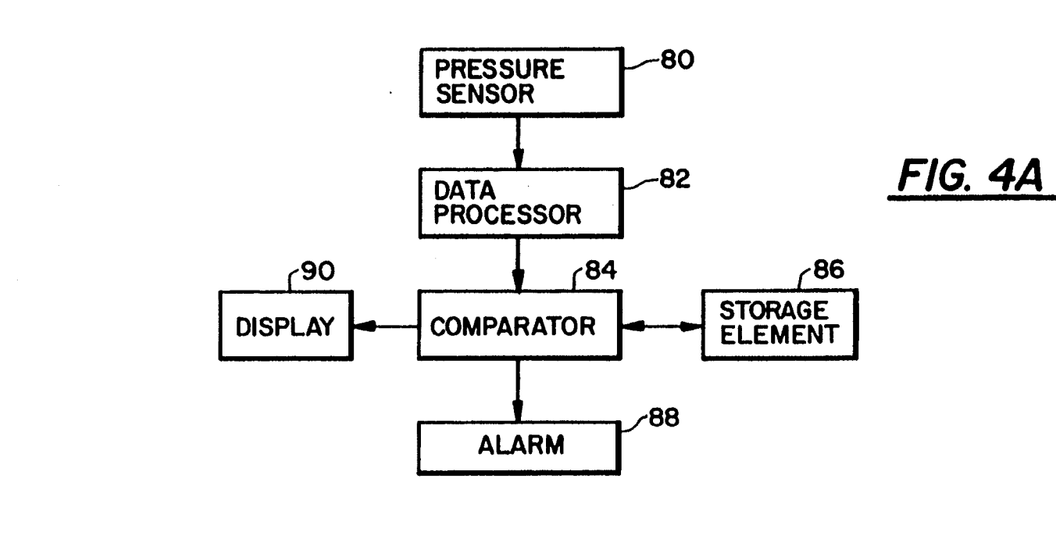
FIG. 4A is a block diagram showing an arrangement of a peak flow meter embodying the principles of the present invention.

Referring now to FIG. 4A, the peak flow meter is provided with circuitry for comparing measured PEFR results with a specified value. The circuitry includes pressure sensor 80 which detects a pressure rise within the conduit of a peak flow meter and generates an electrical signal corresponding to the magnitude of the pressure rise. Data processor 82, in response to the electrical signal, converts the analogue signal into a digital measurement or data result. Comparator 84 compares this data result with a specified value stored in storage element 86. The specified value may, for example, be a fixed reference data result corresponding to a predetermined fixed peak expiratory flow rate, such as a peak expiratory flow rate established when the patient is healthy. Alternatively, the specified value may be a variable dependant upon one or more data results previously derived by data processor 82. For example, such variable may be an average of a predetermined number of previously attained peak expiratory flow rates or may be simply equivalent to the previously attained peak expiratory flow rate.

When comparator 84 determines that a data result is a predetermined amount lower than the specified value, alarm 88 is enabled and provides an indication to the subject that immediate medical attention may be required. It is appreciated that the aforementioned predetermined amount may be equivalent to zero, so that alarm 88 is enabled whenever a data result is below the specified value.

Alarm 88 may comprise an audio and/or visual indicator. A display 90 may also be included to provide a visual read-out of data results.

Figure 4B:
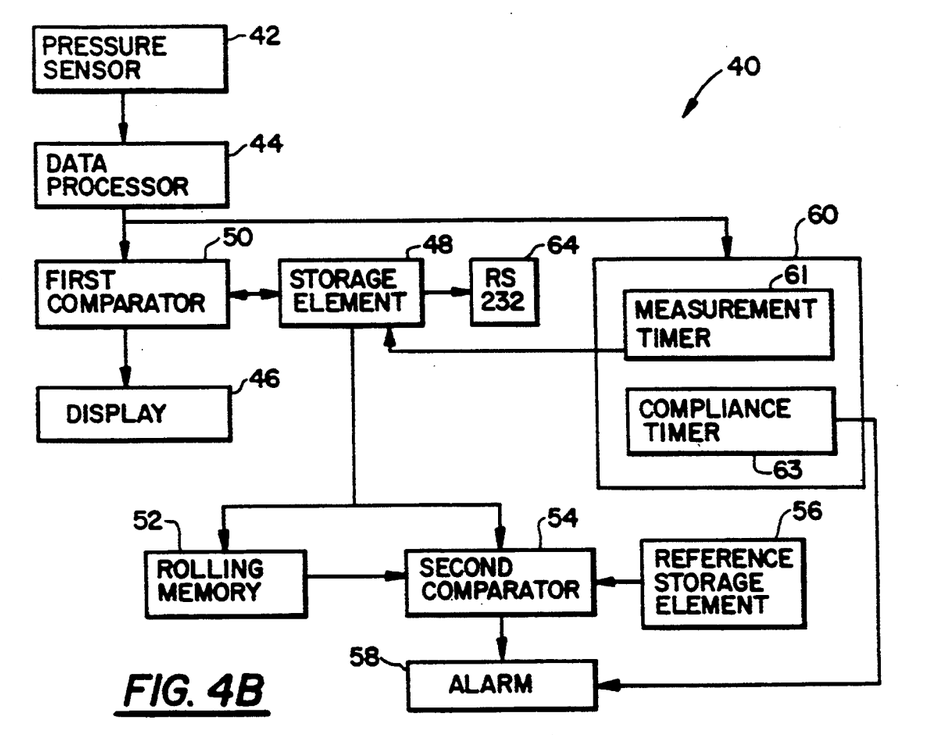
FIG. 4B is a block diagram showing an arrangement of a peak flow meter embodying the principles of the present invention.

Referring now to FIG. 4B, a flow diagram is shown generally at 40 representing the logical electrical processing circuitry of another embodiment of the present invention.

Since PEFR is the greatest flow velocity that can be obtained during forced expiration, it is advantageous to take several measurements in establishing an accurate PEFR evaluation. Thus, in this embodiment, before comparing an established peak expiratory flow rate to either a fixed or variable specified value, a set of several measurements may be taken, the best of which is then compared.

In this embodiment, pressure sensor 42 detects a pressure rise within the conduit of a peak flow meter, such as conduit 12 shown in FIG. 1, when a subject blows therein. Pressure sensor 42 generates an electrical signal corresponding to the magnitude of the pressure rise. Data processor 44, in response to the electrical signal generated by pressure sensor 42, converts the analogue signal into a useful digital measurement or data result.

A first comparison is accomplished by first comparator 50 and storage element 48 in order to obtain a best data result corresponding to the best PEFR attained within a set of PEFR measurements. To accomplish this, data processor 44 provides its digital output to first comparator 50, which compares each data result to the preceding data result, which has been previously stored in storage element 48. If the data result is the first data result received by the peak flow meter within a set of blows, it will be stored by storage element 48 without such comparison. After performing each comparison, first comparator 50 sends the greater of the two data results back into storage element 48 until the next data result is received. The output of first comparator 50 also sends the greater of the two data results to display 46, typically an LED (light emitting diode) display, which displays the prevailing data result within the present set of blows. After a set of data results has been completed, an ultimately prevailing best data result is achieved. In the broadest aspects of the present invention, it is appreciated that storage element 48 may store all data results within a given set, and comparator 50 may then undertake one comparison of all data results stored in storage element 48 in determining the best data result among them.

The number of data results constituting a set for which data results will be compared may either be a predetermined fixed number or a varying number. In the most preferred embodiment, the number of data results which will be compared is equal to the number of times the subject blows into the conduit before the subject finally fails to blow into the conduit within a predetermined period of time. For example, if the predetermined period of time is one minute, storage element 48 will continue to accept data readings to be compared so long as the subject continues to blow into conduit 12 within one minute after previously blowing into the conduit. Once one minute elapses without the subject blowing into the conduit, a best data result is derived for that set of blows.

A timer 60, comprising measurement timer 61, is provided to time the interval between each blow. In the most preferred embodiment, measurement timer 61 receives the signal generated by data processor 44 each time the subject blows into conduit 12. This signal resets the predetermined time period so that the period begins to run anew each time the subject blows into the conduit. When the predetermined time period is finally allowed to lapse, measurement timer 61 generates an enabling signal to storage element 48, indicating to storage element 48 that the data result stored therein is a best data result.

After each best data result is determined, it is then sent to a memory element. In the most preferred embodiment, the memory element is a rolling memory, indicated at 52. Rolling memory 52 stores a predetermined number, typically 5 to 10, of the most recent best data results and expels older best data results.

Each best data result is also sent to second comparator 54, which then determines when a best data result is a predetermined amount lower than a specified value. The specified value may be a variable dependant upon previously attained best data results. In a preferred embodiment, the specified value is an average of previous best data results stored in rolling memory 52. Alternatively, second comparator 54 may compare each best data result to only the preceding best data result stored in rolling memory 52. As a third alternative, each best data result determined by first comparator 50 may be compared, in second comparator 54, to one or more reference data results stored in reference storage element 56. It is appreciated that second comparator 54 may compare each best data result to any one, or any combination, of the three aforementioned alternatives. Then, when second comparator 54 determines that a best data result is a predetermined amount below the specified value, alarm 58 is enabled. It is appreciated that the aforementioned predetermined amount may equal zero.

In the broadest aspects of the present invention, more than one reference data result may be provided in reference storage element 56. For example, one reference data result may correspond to a peak expiratory flow rate which indicates that the subject's respiratory condition is just slightly below normal. When any best data result is lower than this reference data result, second comparator 54 generates a signal to alarm 58 which provides an indication (i.e., a single audio "beep") that the subject is in such condition so that the appropriate action can be taken (i.e., use an asthma inhaler). A second reference data result may then also be provided in reference storage element 56 to indicate, for example, a more serious respiratory condition. Second comparator 54, indicating this more serious condition when a best data result is below this second reference data result generates an appropriate signal to alarm 58, which then provides an indication distinguishable from the indication generated at the less serious condition (i.e., two audio "beeps"). Alarm 58 may provide any type of alerting indication, such as an audio alarm, an LED indication, a color light display, or any combination thereof.

Timer 60 also comprises a compliance timer 63, which provides an enabling signal to alarm 58 if the subject does not blow into conduit 12 after a predetermined time period since the subject last blew into conduit 12. The enabling signal generated by compliance timer 63 enables alarm 58 to provide the respiratory patient an indication that he or she is due for a peak expiratory flow rate evaluation and should blow into conduit 12. The typical predetermined time period is on the order of 24 hours, but that period may change significantly according to the severity of the patient's condition. Thus, compliance timer 63 can be adjusted to set the predetermined time period.

Alarm 58 may incorporate an audio and/or visual indication which is enabled if the patient fails to undergo a peak expiratory flow rate evaluation within a predetermined time period since the patient's last peak expiratory flow rate evaluation. Such an alarm may be provided in conjunction with any type of peak flow meter, regardless of the manner in which the flow meter accomplishes its function (i.e., mechanically or electrically).

Each time a subject blows into conduit 12, the signal generated by data processor 44 automatically resets compliance timer 63. As a result, alarm 58 will not be enabled if the subject blows into conduit 12 before the predetermined time period expires, and only after compliance timer 63 is allowed to reach the predetermined time period will alarm 58 be enabled. Therefore, so long as a subject continues to comply with the regular use of the peak flow meter by blowing into conduit 12 at regularly spaced time intervals which are less than the predetermined time period, compliance timer 63 will not generate an enabling signal to alarm 58.

If the predetermined time period should lapse, thereby causing alarm 58 to be enabled, the subject can disable alarm 58 by simply blowing into conduit 12. This is accomplished as the electrical signal generated by data processor 44 also serves to disable alarm 58. In the broader aspects of the present invention, other means of disabling alarm 58 can be provided, such as a manual switching mechanism. The same type of switching mechanism can also be used to manually reset compliance timer 63 if desired. Such a manual reset can be in place of the above described automatic reset of compliance timer 63 or can be provided in addition thereto. Furthermore, in the broader aspects of the present invention, it is appreciated that when provided with the automatic reset, compliance timer 63 may receive a resetting signal directly from pressure sensor 42 rather than from data processor 44.

The peak flow meter may also include a means for communicating best data results to a remote location. Preferably, the best data results are transmitted over a telephone line where they are received by medical personnel who can assess the data. However, the data results may be transmitted to any external receiver. To accomplish this, a transmitting device 64 receives best data results from storage element 48 and is capable of transmitting digital data over a communication line when a receiver is available on the other end. Typically, an RS-232 chip, such as the MAX233A device manufactured by Maxim Integrated Products, is used for accomplishing this function.

In the broader aspects of the present invention, it is appreciated that several permutations of the inter-relation between pressure sensor 42, data processor 44, first comparator 50, storage element 48, display 46, rolling memory 52, second comparator 54, storage element 56, alarm 58, and timer 60 are possible in accomplishing the same result.

Figure 5:
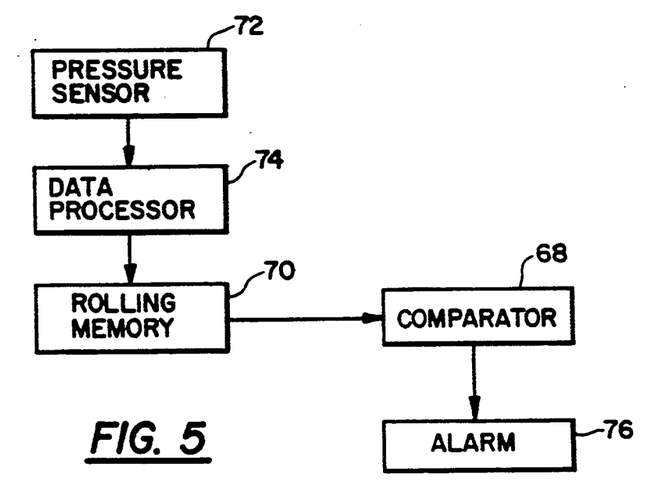
FIG. 5 is a block diagram showing an arrangement of a peak flow meter embodying the principles of the present invention.

Referring now to the peak flow meter embodied in FIG. 5, an incentive is provided to induce the subject to exceed the preceding PEFR result within a set of PEFR measurements.

In this embodiment, pressure sensor 72 detects a pressure rise within the conduit of a peak flow meter, such as conduit 12 shown in FIG. 1, when a subject blows therein. Pressure sensor 72 generates an electrical signal corresponding to the magnitude of the pressure rise.

Data processor 74, in response to the electrical signal generated by pressure sensor 42, converts the analogue signal into a useful digital measurement or data result. A comparator 68 is provided for comparing successive data results stored in rolling memory 70. Comparator 68 generates a greater indication signal when the most recent data result is greater than a preceding data result. Alarm 76, in response to a greater indication signal, generates an indication that the most recent data result is greater than the aforementioned preceding data result. Alarm 76 may comprise a visual display, a tone generator, or a combination thereof.

Comparator 68 may also be capable of generating a lower indication signal when the most recent data result is lower than that of a preceding data result. Alarm 76 is responsive to and capable of differentiating between the greater indication signal and the lower indication signal for indicating to the subject whether a most recent data result is greater or less than the preceding data result in question.

It will be realized that the foregoing preferred specific embodiments have been shown and described for the purpose of this invention and are subject to change without departure from such principles. The invention includes all modifications encompassed within the spirit and scope of the following claims.

What is claimed is:

1. A peak flow meter comprising:
   a conduit through which air can be blown by a subject, said conduit having a restriction therein for causing air blown into said conduit to escape said conduit at a restricted rate therefrom and create a pressure rise therein;
   pressure sensing means for generating an electrical signal corresponding to said pressure rise within said conduit each time the subject blows into said conduit;
   data processing means for processing each said electrical signal and for deriving data results corresponding to peak expiratory flow rates of air blown into said conduit for any number of blows by the subject;
   first comparison means having a memory for storing said data results and comparing said data results to one another for said number of blows by the subject to derive a best data result corresponding to a best peak expiratory flow rate attained by the subject in said number of blows;
   second comparison means for comparing said best data result in said number of blows to a specified value and for generating an output signal when said best data result is a predetermined amount lower than said specified value; and
   alarm means, responsive to said output signal, for generating an indication when said best data result is said predetermined amount lower than said specified value.

2. A peak flow meter as claimed in claim 1, further comprising:
   third comparison means for comparing each data result to at least one preceding data result derived by said data processing means and for generating a greater indication signal when a most recent data result is greater than said preceding data result; and
   indication means, responsive to said greater indication signal, for indicating that the most recent data result is greater than said preceding data results.

3. A peak flow meter as claimed in claim 1 wherein said second comparison means comprises memory means for storing said specified value, said specified value being a predetermined reference data result.

4. A peak flow meter as claimed in claim 1 wherein said first comparison means expels a data result previously stored therein when a subsequent data result is greater than said previously stored data result, said subsequent greater data result being stored in said first comparison means in place of said previously stored data result.

5. A peak flow meter as claimed in claim 1 wherein said second comparison means comprises memory means for storing a plurality of previously derived best data results, and wherein said specified value is a variable dependent upon at least one of said previously derived best data results stored in said memory means.

6. A peak flow meter as claimed in claim 5 wherein said memory means comprises a means for recording a date and time of each said best data result stored therein.

7. A peak flow meter as claimed in claim 1 wherein said second comparison means comprises a rolling memory for storing a predetermined number of previously derived best data results and wherein said specified value is a variable dependent upon at least one of said best data results previously derived and stored in said rolling memory.

8. A peak flow meter as claimed in claim 1 further comprising means for measuring a period of time between blows by the subject, and wherein said number of blows is equivalent to a number of instances the subject has blown into said conduit when the subject fails to blow into said conduit after a predetermined period of time.

9. A peak flow meter as claimed in claim 1 wherein said pressure sensing means, said data processing means, said first comparison means, said second comparison means and said alarm means are contained in a housing separable from said conduit.

10. A peak flow meter as claimed in claim 9 wherein said conduit comprises means for storing said housing when said peak flow meter is not in use.

11. A peak flow meter as claimed in claim 1 further comprising a means for transmitting said best data results to a remote location.

12. A peak flow meter providing a prompt for facilitating a subject's compliance with the periodic use thereof comprising:
    a conduit through which air can be blown by a subject;
    means for evaluating a peak expiratory flow rate attained by the subject when the subject blows into said conduit;
    indicating means for indicating that the subject is due for said peak expiratory flow rate evaluation when the subject fails to blow into said conduit after a predetermined time period since the subject's last peak expiratory flow rate evaluation; and
    means for discontinuing the indication in response to the subject's compliance with the use of the peak flow meter by blowing into the conduit in a manner sufficient to permit the evaluating means to evaluate the peak expiratory flow rate of the subject.

13. A peak flow meter as claimed in claim 12 further comprising timing means for measuring said predetermined time period.

14. A peak flow meter as claimed in claim 13, further comprising means for resetting said timing means so that said predetermined time period begins to run anew, and wherein said means for discontinuing said indication and said resetting means are actuated when the subject blows into said conduit in a manner sufficient to permit the evaluating means to evaluate the peak expiratory flow rate of the subject.

15. A peak flow meter as claimed in claim 12 wherein said indicating means comprises timing means for measuring said predetermined time period and alarm means generating an alarm when the subject fails to blow into said conduit after said predetermined time period.

16. A peak flow meter as claimed in claim 15 wherein said timing means comprises means for adjusting said predetermined time period.

17. A peak flow meter as claimed in claim 15 wherein said alarm means is at least one of a tone generator and a visual display.

18. A peak flow meter comprising:
a conduit through which air can be blown by a subject, said conduit having a restriction therein for causing air blown into said conduit to escape at a restricted rate therefrom and create a pressure rise therein;
pressure sensing means for generating an electrical signal corresponding to said pressure rise within said conduit each time the subject blows into said conduit;
data processing means for processing each said electrical signal and for deriving data results corresponding to peak expiratory flow rates of air blown into said conduit for any number of blows by the subject;
comparison means for comparing each data result to at least one preceding data result derived by said data processing means and for generating a greater indication signal when a most recent data result is greater than said preceding data result; and
indication means, responsive to said greater indication signal, for indicating that the most recent data result is greater than said preceding data result.

19. A peak flow meter as claimed in claim 18 wherein said comparison means generates a lower indication signal when the most recent data result is lower than that of preceding data result, said indication means responsive to, and capable of differentiating between, said greater and said lower indication signals for indicating to the subject whether the most recent data result is greater or less than said preceding data result.

20. A peak flow meter as claimed in claim 19 wherein said comparison means further comprises rolling memory means for storing a predetermined number of said successive data results.

21. A peak flow meter as claimed in claim 20 wherein said indication means is at least one of a tone generator and a visual display.

22. A peak flow meter as claimed in claim 18, wherein said preceding data result compared to said most recent data result by said comparison means is a data result which immediately precedes said most recent data result, and wherein said indication means, responsive to said greater indication signal, indicates when the most recent data result is greater than said immediately preceding data result.

23. A peak flow meter comprising:
a conduit having an inlet through which air can be blown by a subject, said conduit having a restriction therein for causing air blown into said conduit to escape at a restricted rate therefrom and create an air pressure rise therein, said conduit including a flexible element which flexes in response to said pressure rise in said conduit; and
peak expiratory flow measuring means cooperable with said conduit for deriving a peak expiratory flow rate of said subject, said peak expiratory flow measuring means including: i) a pressure transducer having a chamber defining an inner air space, said pressure transducer being capable of measuring air pressure within said chamber and generating a signal based upon said air pressure within said chamber, and ii) circuitry means responsive to said signal for deriving said peak expiratory flow rate of said subject;
said peak expiratory flow measuring means being cooperable with said conduit in a manner such that: i) said peak expiratory flow measuring means being selectively separated from and reattached to said conduit so that said conduit is adapted to be sterilized as a separate unit, ii) said flexible element of said conduit can be brought into airtight communication with said inner air space within said chamber to prevent external air from entering said chamber, and iii) flexing of said flexible element towards said inner air space of said chamber creates a pressure rise in said chamber corresponding to the pressure rise in said conduit thereby enabling said pressure transducer to generate said signal as a function of the pressure rise within said conduit so that said circuitry means can derive said peak expiratory flow rate of said subject through said conduit.

24. A peak flow meter as claimed in claim 23 wherein said flexible element seals an opening within said conduit.

25. A peak flow meter as claimed in claim 24 wherein said seal is airtight.

* * * * *